United States Patent [19]

Geary

[11] Patent Number: 5,090,954
[45] Date of Patent: Feb. 25, 1992

[54] SUBCUTANEOUS ACCESS DEVICE FOR PERITONEAL DIALYSIS

[76] Inventor: Gregory L. Geary, 12355 N.W. Maple Hill La., Portland, Oreg. 97229

[21] Appl. No.: 702,775

[22] Filed: May 17, 1991

[51] Int. Cl.$^5$ .............................................. A61M 1/00
[52] U.S. Cl. ........................................ 604/29; 604/49; 604/93; 604/175
[58] Field of Search ............... 604/175, 93, 167, 173, 604/180, 247, 256, 28, 29, 49, 51, 86, 88

[56] References Cited

U.S. PATENT DOCUMENTS

| | | |
|---|---|---|
| 4,160,454 | 7/1979 | Foux . |
| 4,184,497 | 1/1980 | Kolff et al. . |
| 4,256,102 | 3/1981 | Monaco . |
| 4,400,169 | 8/1983 | Stephen . |
| 4,405,305 | 9/1983 | Stephen et al. . |
| 4,490,137 | 12/1984 | Moukheibir .................... 604/175 X |
| 4,559,033 | 12/1985 | Stephen et al. . |
| 4,710,167 | 12/1987 | Lazorthes ............................ 604/175 |
| 4,778,452 | 10/1988 | Moden et al. . |
| 4,781,695 | 11/1988 | Dalton . |
| 4,784,646 | 11/1988 | Feingold . |
| 4,802,885 | 2/1989 | Weeks et al. . |

FOREIGN PATENT DOCUMENTS 119596  3/1984  European Pat. Off. .

Primary Examiner—John D. Yasko
Attorney, Agent, or Firm—Kolisch, Hartwell, Dickinson, McCormack & Heuser

[57] ABSTRACT

A subcutaneous access device for connection to a peritoneal dialysis catheter which includes an elongate housing having a needle-impervious outer shell forming the sides and bottom of the housing. The housing further includes a top expanse which is connected at its periphery to the outer shell and is composed of a needle-permeable and self-sealing material. The expanse has an expansive flat presentation region which extends substantially the length and breath of the housing. A hollow central chamber, disposed intermediate the top expanse and the bottom of the shell, extends the length of the housing. A fitting projects outwardly from the housing and is positioned to accommodate connection with an implanted peritoneal dialysis catheter.

8 Claims, 1 Drawing Sheet

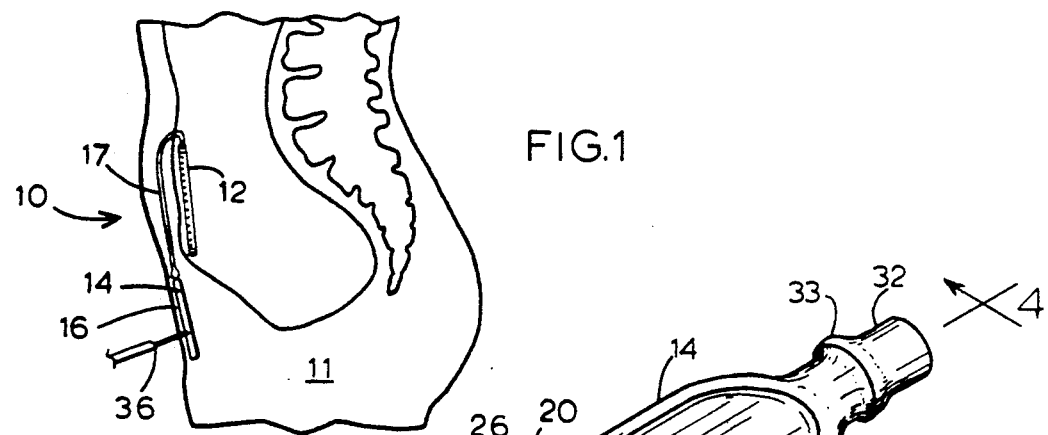
FIG. 1
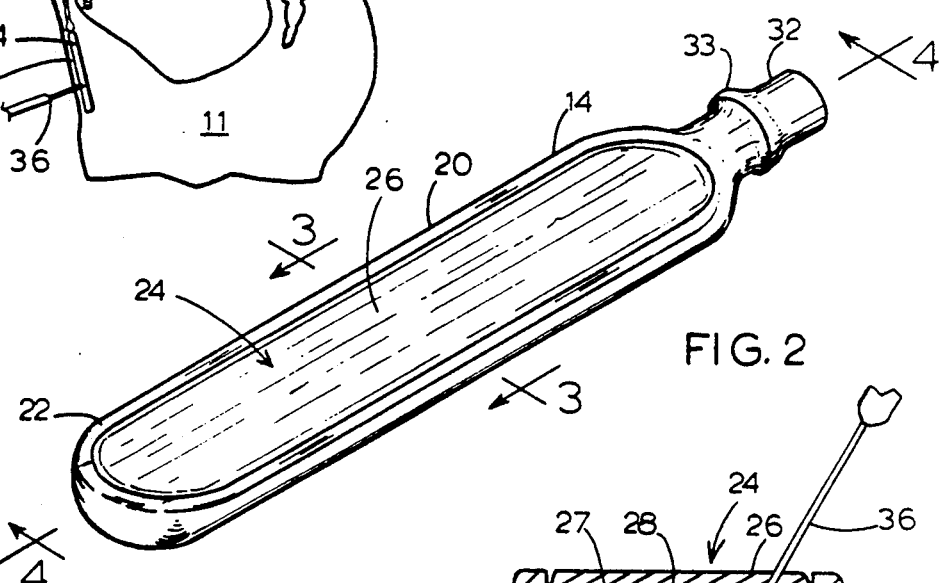
FIG. 2
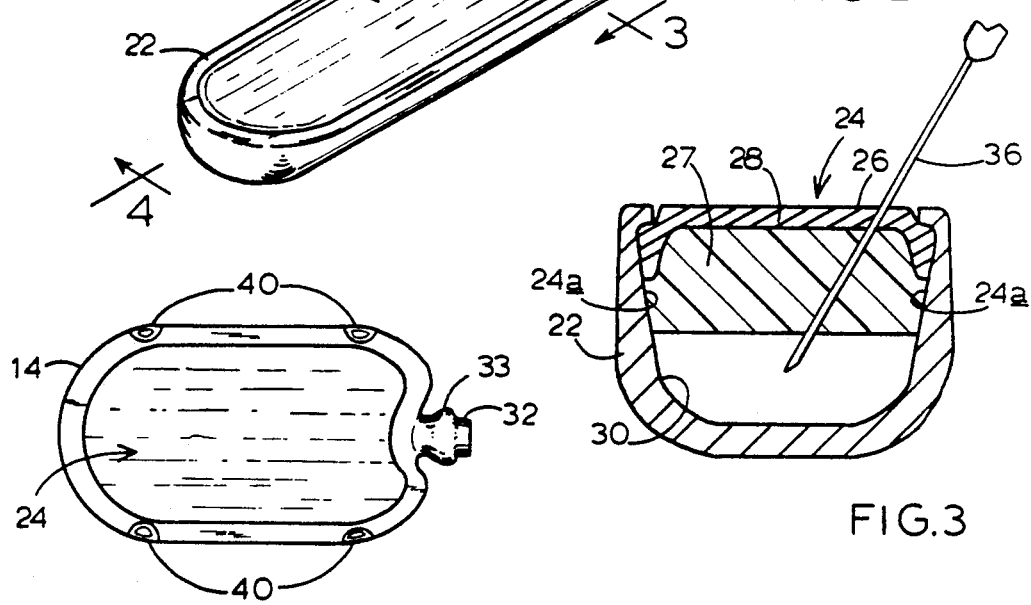
FIG. 3
FIG. 5
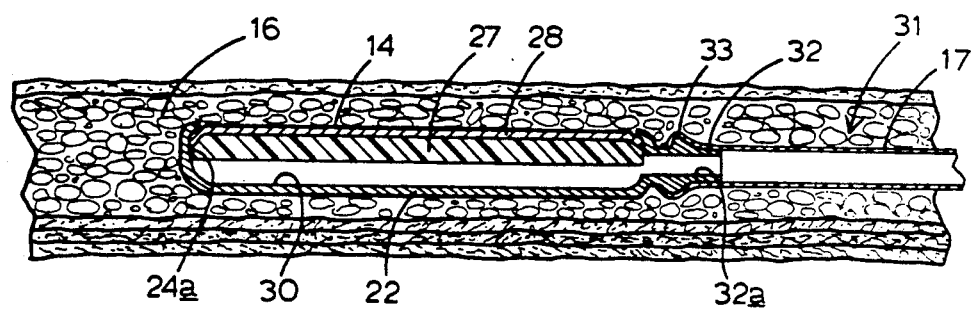
FIG. 4

SUBCUTANEOUS ACCESS DEVICE FOR PERITONEAL DIALYSIS

BACKGROUND AND SUMMARY OF THE INVENTION

This invention relates to a dialysis device and, more particularly, to an implantable subcutaneous device which is connected to an implanted peritoneal dialysis catheter and can be accessed percutaneously with a needle for performing fluid exchanges for peritoneal dialysis.

Presently, peritoneal dialysis is most commonly performed by using the Tenckhoff system that employs a dialysis catheter which has one end permanently implanted within the patient's peritoneal cavity. The other end of the catheter exits externally through the skin in the patient's abdomen, terminating in a section of tubing approximately 10 centimeters in length which is connected during dialysis to dialysate fluid. When the external portion of the catheter is not in use, it is curled on itself and taped to the skin.

There are numerous disadvantages to use of the Tenckhoff system which are primarily caused by having a portion of the catheter external to the patient's skin. First, the external portion of the catheter requires daily wound care at its exit site on the abdomen. Second, the presence of an external access device promotes infections both at the exit site and at the connector areas. Catheter exit site infections are directly caused by having the catheter exit through the skin, which area is chronically contaminated with bacteria. Episodes of peritonitis may also be caused due to break in the sterile technique at the catheter connector areas. Treatment of peritonitis necessitates an expensive drug regime to resolve the infection and, in extreme cases, may require removal of the catheter implant. Another problem with the use of an external catheter is that it causes a negative body image. Patients find them unsightly and embarrassing.

Foux U.S. Pat. No. 4,160,454 discloses an implantable catheter system which includes an elongate hollow casing 2 made of a material such as silastic rubber, that is implanted in the subcutaneous tissue of a patient. Extending generally at a right angle from one end of casing 2 is a tube 26, the interior of which communicates with the interior of casing 2 and is of sufficient length so that when casing 2 is implanted subcutaneously, tube 26 may extend into the peritoneal cavity of the patient. To provide rigidity, casing 2 is reinforced by a coil of wire 34 (shown by dotted line in FIG. 1) made of a material such as stainless steel.

There are numerous disadvantages, however, with the Foux device. First, because of the shape of Foux, only a small surface area of the device adjacent the patient's skin is presented for needle penetration. Because there is only a small skin area available for sticking, the area would not be allowed to heal before that area would need to be repunctured. Second, casing 2 appears to be cigar-shaped and substantially circular in cross section, such that correct placement of a needle into the interior of the device would be difficult because casing 2 would tend to rotate or move and would be difficult to pin down or stabilize just prior to needle penetration. With Foux, it would be difficult for the user to confirm whether the needle is in the proper position for fluid exchanges. Both because of the shape of the device and because it is reinforced only with a wire coil, it would be very easy for a needle to penetrate through the entire device and out the other side. Furthermore, Foux presents a unitary system which includes the subcutaneous access device as well as the peritoneal catheter and is not designed to be utilized with a previously implanted peritoneal dialysis catheter.

Accordingly, a general object of the present invention is to provide an access device that is located internally in the patient's subcutaneous tissue thereby eliminating the need for an external catheter and the problems associated therewith.

Another object is to provide a device with a large presentation area which can be easily accessed by the patient.

A further object is to provide an access device which is designed to facilitate correct needle placement and to give the patient prompt confirmation that the needle is correctly positioned.

Yet a further object of the present invention is to provide an access device which is suitable for repeated entries.

Yet another object is to provide a subcutaneous access device which can be retrofitted with a previously implanted peritoneal dialysis catheter.

In the present invention, there is provided a subcutaneous access device for connection to a peritoneal dialysis catheter which includes an elongate housing having a needle-impervious outer shell forming the sides and bottom of the housing. The housing further includes a top expanse connected at its periphery to the outer shell, which expanse is composed of a needle-permeable and self-sealing material and has extending substantially the length and breadth of said housing an expansive flat presentation region. A hollow central chamber, disposed intermediate the top expanse and the bottom of the shell, extends the length of the housing. The housing also includes a fitting which projects outwardly from the housing and is positioned to accommodate connection with an implanted peritoneal dialysis catheter.

BRIEF DESCRIPTION OF THE DRAWINGS

The foregoing objects and advantages of the present invention will be more clearly understood when considered in conjunction with the accompanying drawings, wherein:

FIG. 1 is a schematic illustration of the system of the present invention implanted in a patient's abdominal wall;

FIG. 2 is a perspective view of the subcutaneous access device of the present invention;

FIG. 3 is a cross-sectional view taken generally along the line 3—3 of FIG. 2;

FIG. 4 is a cross-sectional view taken generally along the line 4—4 of FIG. 2, on a smaller scale, showing the access device in the intended implanted state in the subcutaneous tissue of a patient; and FIG. 5 is a plan view of a modification of the device of the present invention.

DETAILED DESCRIPTION OF THE PREFERRED EMBODIMENT

Referring to the drawings, shown generally at 10 in FIG. 1, is the peritoneal dialysis system of the present invention, as implanted in the abdomen of a patient, such as patient 11. System 10 includes a peritoneal dialysis catheter 12, such as the Tenckhoff type catheter illustrated in FIG. 1, and an access device 14 implanted in the subcutaneous tissue, shown generally at 16, in the abdomen of patient 11. A tube 17 connects catheter 12 and device 14. Device 14 may be used with other types of peritoneal dialysis catheters than the Tenckhoff. For example, it may be used with the Lifecath ® Peritoneal Catheter Implant.

Turning now to FIGS. 2-4, device 14 includes an elongate housing 20 which has a needle-impervious shell 22 forming the sides and bottom of housing 20. Shell 22 may be constructed of a metal, such as titanium, or of a hard plastic material. The purpose of shell 22 is to provide a surface that stops a needle, such as needle 36, from penetrating. Shell 22 also provides a rigid surface which makes device 14 easily felt under the skin to aid in needle placement.

Device 14 further includes a top expanse, shown generally at 24, which is connected along its periphery 24a to shell 22. Expanse 24 provides an expansive flat presentation region 26 which extends substantially the length and breadth of housing 20. Top expanse 24 includes a relatively thick lower layer 27 which is constructed of a needle-permeable and self-sealing elastomer material, such as silicone rubber.

By providing expansive flat presentation region 26, a patient is presented with a large area for needle penetration. Also, because the surface of region 26 is flat, it is much easier for a patient to hold device 14 in place by pressing the thumb and forefinger of his/her hand down against the region of the skin which is to be stuck with a needle. In addition, because region 26 is flat, device 14 is much more stable under the skin and is much less likely to rotate or twist around while the patient is trying to stick a needle through device 14.

In the preferred embodiment, top expanse 24 further includes an upper layer 28 of a rough or porous material which promotes adhesion and growth of the patient's tissue thereto. Materials which have been found satisfactory for upper layer 28 are Gore-tex ®, polyester resin velour, porous or expanded PTFE (polytetrafluoroethylene), or other similar porous or rough type materials into which tissue can grow. Adhesion of the surrounding tissue to layer 28 further serves to hold device 14 in place. This is important because when the patient sticks a needle into device 14, if device 14 is anchored down through tissue adhesion, it makes it much easier for the patient efficiently to stick the needle into the device. By using layer 28, skin will form scar tissue into expanse 24 so that, upon removing a needle after accessing device 14, there will be less chance of the device moving around and therefore less chance of leaking of peritoneal fluid. If layer 28 was not present, then, when the needle was removed, it would be more likely for device 14 to move around thereby promoting leaking of peritoneal fluid under the skin.

Device 14 further includes a hollow chamber 30 disposed intermediate top expanse 24 and the bottom of shell 22, and extends the length of housing 20.

Shown generally at 31 is means connecting catheter 12 and device 14. Means 31 includes a fitting 32 projecting outwardly from housing 20 with an opening 32a disposed therein through which fluids flow into or out of chamber 30. Means 31 further includes tubing 17 which has one end sleeved over the open end of fitting 32 and the other end of tubing 17 connected to catheter 12. Fitting 32 has a shoulder or ridge 33 over which tubing 17 is passed and then sutured down around.

FIG. 5 illustrates a modification of access device 14 which further includes suture rings, such as rings 40, disposed in shell 22. During implantation of device 14, the physician would further secure device 14 in position by suturing device 14 through rings 40 to the patient's tissue.

One of the advantages of access device 14 of the present invention is that it is designed for use with a previously implanted peritoneal catheter as well as for use with a catheter which is implanted at the same time device 14 is being implanted. Thus, device 14 can be used with a new catheter as well as a preexisting catheter.

Device 14 is surgically placed under the skin, in the subcutaneous tissue, on the patient's abdomen in a procedure that requires only local anesthesia or light sedation, and does not require general anesthesia. Device 14 is positioned so that the interior of chamber 30 may be accessed by placing a needle, which is connected to tubing attached to dialysis fluid, through the skin into the chamber. Once the needle is within chamber 30, dialysis may be performed by fluid exchanges. When dialysis is completed, the needle is removed.

One of the advantages of the design device 14 is that by having a flat expansive presentation region 26, a substantial surface area is presented for ease of needle access. Also, by having an expansive region, a larger skin surface can be utilized for needle penetration so as to allow healing of stick sites between use, thereby avoiding deterioration of that region of the skin. Furthermore, because of the construction of device 14, a patient or helper can easily feel the device under the skin so that needle access can be performed with relative ease. Also, because device 14 has an expansive flat surface 26, it can be stabilized with one hand while the access needle is being placed into device 14 with the other hand. The design of device 14 facilitates proper placement of the needle because as the needle goes through upper expanse 24 and enters chamber 30, if it goes too far, it hits rigid shell 22, which can be felt by the person using the needle. Also, proper placement of the needle is confirmed by flow of dialysis fluid.

Another advantage which is realized by the present invention is that adequate flows of fluid, both in-flow and out-flow, are obtainable to permit effective dialysis.

It is anticipated that use of the system of the present invention will result in more patients accepting peritoneal dialysis instead of the much more costly procedure of hemodialysis. Based on national cost figures comparing hemodialysis versus peritoneal dialysis, there is an anticipated cost savings of $7,000.00 to $10,000.00 per year per patient for basic dialysis requirements. Additional savings will be realized from the system of the present invention in that there will be a lower rate of infection as compared to peritoneal dialysis using external devices, and reduced profession services will be realized.

While a preferred embodiment of the invention has been described, obviously variations and modifications are possible without departing from the spirit and scope of the present invention.

It is claimed and desired to secure by Letters Patent:
1. A system for peritoneal dialysis comprising:
an implantable intraperitoneal dialysis catheter,
an elongate subcutaneous access device, said device including a rigid needle-impervious shell of elongate outline and having a bottom and upstanding sides, a top expanse providing an expansive flat presentation region forming the top of the access device, said expanse being formed of a layer of needle-permeable elastomer material and said layer being lodged within said shell with the outer perimeter of said layer confined within the sides of the shell and with the base of the layer spaced upwardly from the bottom of the shell, the layer having a thickness substantially exceeding the thickness of the sheet, the perimeter of the layer and the sides of the shell having an interacting construction serving to limit movement of the layer downwardly within the shell toward said bottom, a hollow central chamber being defined intermediate said layer and the bottom of said shell which chamber extends the length of the device, and means connecting said catheter and said device.

2. The system of claim 1, wherein the sides of the shell converge on each other progressing toward said bottom and said layer has sides that incline toward each other forming the perimeter of the layer and said layer wedges within the shell to prevent movement of the layer downwardly toward said bottom of the shell.

3. The system of claim 2, wherein said shell further includes portions joined to the sides of the shell that overlie a top margin of said top expanse to prevent displacement of the top expanse upwardly from said bottom.

4. The system of claim 2, wherein said needle-impervious shell is made of a metal.

5. The system of claim 2, wherein said needle-impervious shell is made of a hard plastic.

6. The system of claim 2, wherein said expanse comprises silicone rubber.

7. The system of claim 6, wherein said top expanse further includes an upper layer of material which promotes growth adhesion of animal tissue thereto.

8. A subcutaneous access device for connection to a peritoneal dialysis catheter comprising:

an elongate needle-impervious shell having a bottom and upstanding sides, a top expansive having an expanse flat presentation region extending substantially the length and width of said shell, said top expanse being formed of a layer of needle-permeable elastomer material lodged within said shell with the perimeter of said layer confined within the sides of the shell and with the base of the layer spaced from the bottom of the shell, the base of said layer and the bottom of the shell defining between them an elongate chamber extending the length of the shell, the layer having a thickness substantially exceeding the thickness of the shell, the sides of the shell converging on each other progression toward said bottom and said layer having sloping sides forming its perimeter and said layer wedging within the shell to limit movement of the layer toward said bottom of the shell, said shell including portions joined to the sides of the shell that overlie the layer to prevent displacement of the layer upwardly and away from the shell, and a fitting joined to and projecting outwardly from the shell positioned to accommodate connection with an implanted peritoneal dialysis catheter.

* * * * *